United States Patent [19]

Hashimoto et al.

[11] Patent Number: 5,120,641
[45] Date of Patent: Jun. 9, 1992

[54] METHOD FOR MEASUREMENT OF SEROTONIN UPTAKE SITES AND RADIOLIGAND THEREFOR

[75] Inventors: Kenji Hashimoto, 4-1-39-604, Okinouemachi, Fukuyama-shi, Hiroshima; Tsuyoshi Goromaru, Fukuyama, both of Japan

[73] Assignees: Daiichi Pure Chemicals Co., Ltd.; Tokyo; Kenji Hashimoto, Hiroshima, both of Japan

[21] Appl. No.: 633,676

[22] Filed: Dec. 26, 1990

[30] Foreign Application Priority Data

Dec. 27, 1989 [JP] Japan .................. 1-339075

[51] Int. Cl.$^5$ ............. G01N 23/00; C07D 401/00; C12Q 1/00
[52] U.S. Cl. .................. 435/7.21; 436/57; 436/501; 544/363
[58] Field of Search .............. 424/1.1; 436/57, 501; 544/363; 435/7.21

[56] References Cited

PUBLICATIONS

*Radioisotopes,* vol. 39, No. 4, pp. 168–169.
*Eur. J. Pharmacol.,* 180 (1990) 273–281.
*J. Pharmacol. Exp. Ther.,* 225, No. 1, 146–153.
*Eur. J. Pharmacol.,* 187 (1990) 295–302.
*Fundam. Clin. Pharmacol.,* (1990), 4, 635–641.
Hashimoto, K. et al., "Preparation of [3H]-6-Nitroquipazine . . . Inhibitor", *Radioisotopes,* 39(4), 168–9, 1990 [CA. 114(1): 6442q] (Abstract).

*Primary Examiner*—John B. Maples
*Attorney, Agent, or Firm*—Bacon & Thomas

[57] ABSTRACT

Disclosed herein is an improved method for measurement of serotonin uptake sites in a sample, in which a radioligand is incubated with a sample and then the radioactivity of the radioligand bound to the sample is determined, wherein the improvement comprises using tritium-labeled 6-nitro-2-N-piperazinylquinoline or an acid addition salt thereof as the radioligand.

2 Claims, 3 Drawing Sheets

■—■ : Specific binding
▲—▲ : Nonspecific binding

Amount of Binding (fmole/mg protein)

Inhibition potency of $(^3H)^6$ - nitroquipazine (Log M)

2 : Indalpine
3 : Fluoxetine
4 : Z-Norzimelidine
5 : Imipramine
6 : Amitriptyline
8 : Nortriptyline
10 : Mianserin

METHOD FOR MEASUREMENT OF SEROTONIN UPTAKE SITES AND RADIOLIGAND THEREFOR

BACKGROUND OF INVENTION

1. Field of the Invention

This invention relates to an improved method for measurement of serotonin uptake sites and a radioligand for use in such an analysis.

2. Description of the Background Art

Serotonin is known as a vasoconstrictor material, and is widely distributed in enterochromaffin cells, platelets, central nervous system and other tissues. In addition to the constrictory effects of smooth muscle of blood vessels, uterin, bronchium, intestine or the like, it has been known that serotonin plays an important role as a neurotransmitter in the central nervous system.

In cells that synthesize serotonin, tryptophan which is an amino acid is rapidly hydroxylated to 5-hydroxytryptophan by the enzyme tryptophan-5-hydroxylase, and is then decarboxylated to serotonin by the aromatic L-amino acid decarboxylase. It is known that serotonin is stored therein as a nondiffusable complex formed with adenosine triphosphate in platelets and enterochromaffin cells, and in synaptic vesicles of the central nervous system. Released serotonin undergoes oxidative deamination by monoamine oxidase to form 5-hydroxyindoleacetaldehyde. This is promptly degraded, mainly by further oxidation to 5-hydroxyindoleacetic acid by aldehyde dehydrogenase, and 5-hydroxyindoleacetic acid is excreted in the urine.

It is well known that termination of the effects of serotonin in synaptic function occurs in two ways by an uptake process and by metabolism of the transmitter. Although the details of serotonin metabolism have been clearly established, the process probably plays a minor role in terminating the action of serotonin at the synaptic cleft. The most likely terminating process is the reuptake of serotonin by the presynaptic terminal. Thus, serotonin uptake sites, which exist in the presynaptic nerve terminal, play an important role in regulating the serotonin content in the synaptic cleft. It is, therefore, of great interest to measure the serotonin uptake sites. Interestingly, it has been reported that there is a reduced density of serotonin uptake sites in the brain tissue of depressed patients and Alzheimer's disease. Study of serotonin uptake sites in the brains of people with these diseases is useful for the diagnosis and therapy of these diseases.

Radioreceptor assay has been used as measurement of the serotonin uptake sites. Radioreceptor assay is a method for measuring the radioactivity of a radioligand bound to sample after incubating the radioligand and sample. At present, radioligands such as tritium-labeled imipramine and tritium-labeled paroxetime have been used.

Radioligands used at present do not have high specificity and affinity for serotonin uptake sites in intact tissues, and tritium-labeled imipramine binds other binding sites as well as serotonin uptake sites. Therefore, it is necessary to develop an excellent radioligand having high specificity and high affinity for serotonin uptake sites.

Under the above-described circumstances, the present inventors have conducted extensive studies, and as a result, have found that tritium-labeled 6-nitroquipazine, or an acid thereof, has high specificity and affinity for serotonin uptake sites.

SUMMARY OF THE INVENTION

Accordingly, an object of this invention is to provide a radioligand, tritium-labeled 6-nitro-2-piperazinylquinoline or an acid addition salt thereof, which has a high affinity and high specificity for serotonin uptake sites.

A further object of this invention is to provide an improved method for measuring serotonin uptake sites using tritium-labeled 6-nitro-2-piperazinylquinoline or an acid acid addition salt thereof as a radioligand in measuring the radioactivity bound to serotonin uptake sites after reacting the radioligand and sample.

DETAILED DESCRIPTION OF THE INVENTION AND PREFERRED EMBODIMENTS

Figure 1:
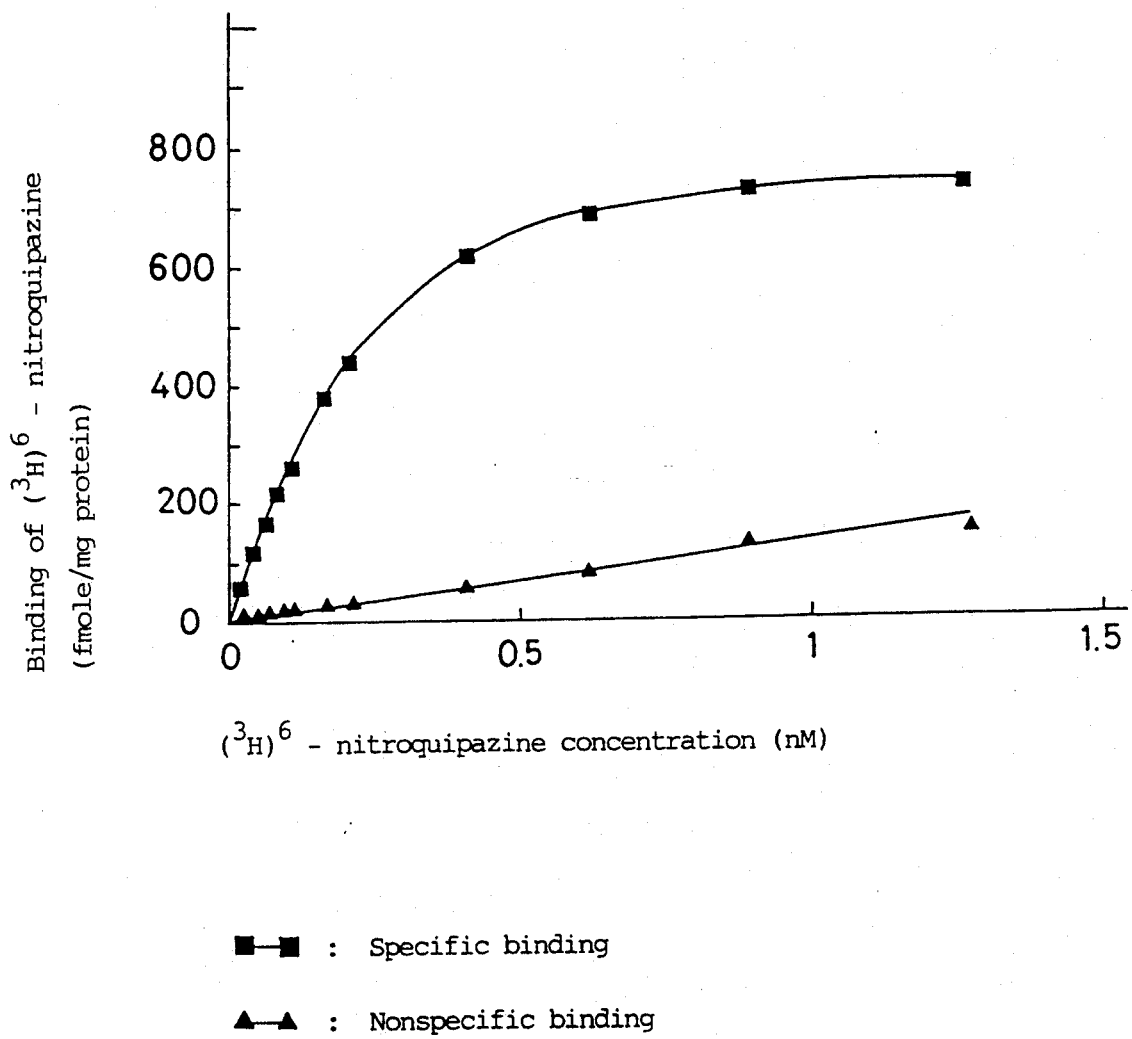
FIG. 1 shows the saturation binding isotherm and non-specific binding of [$^3$H]6-nitroquipazine.

Tritium-labeled 6-nitro-2-piperazinylquinoline or acid addition salts thereof (hereinafter referred to as ([$^3$H]6-nitroquipazine) used as the radioligand in the present invention are those labeled by tritium at one or more position of 6-nitro-2-piperazinylquinoline and acid addition salts of the compound as represented by the following formula:

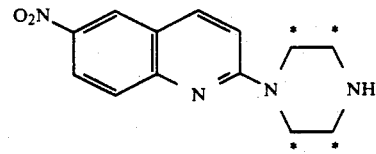

wherein asterisk marks mean positions for tritium.

Suitable acids for the acid addition salts are inorganic acids such as hydrochloric acid, sulfuric acid, nitric acid and the like, as well as organic acids including acetic acid, oxalic acid, citric acid, fumaric acid and the like.

[$^3$H]6-nitroquipazine used in the present invention is prepared by direct nitration of tritium-labeled 2-piperazinylquinoline using a mixture of nitric acid and sulfuric acid or nitronium tetrafluoroborate. Reaction is performed by nitration under normal conditions and [$^3$H]6-nitroquipazine is separated and purified using high performance liquid chromatography.

This radioligand is used as [$^3$H]6-nitroquipazine or acid addition salts thereof, or used as a solution of a suitable buffer, physiological saline and the like.

In order to carry out measurement of serotonin uptake sites according to this invention, conventional methods can be followed except that [$^3$H]6-nitroquipazine or an acid addition salt thereof is used as a radioligand. In other words, according to the method of this invention, a sample is allowed to react (incubation) with the radioligand of the invention, then the radioactivity of the radioligand bound to the sample is measured.

As samples may be mentioned various tissues and cell membranes of animals including human. Examples are tissues of brain, intestine and blood vessel, and platelets. Incubation is carried out in a suitable buffer at 0° to 37° C. for 5 minutes to several hours. The radioactivity of the radioligand bound to the sample is measured by a scintillation counter after unreacted ligand is removed.

EXAMPLES

The invention is hereinafter described by way of examples, which should not be construed as limiting the invention thereto.

EXAMPLE 1

Synthesis of [$^3$H]6-Nitroquipazine

Tritium-labeled 2-N-piperazinylquinoline (position of tritium: piperazinyl group) was dissolved in a mixture of sulfuric acid (0.1 ml) and nitric acid (0.1 ml) and the mixture was allowed to stand at room temperature for 5 minutes. To the reaction mixture was carefully added cold water (0.2 ml), and 50% sodium hydroxide (0.4 ml) in this order. [$^3$H]6-Nitroquipazine was separated and purified by high performance liquid chromatography [column; SHIM-PACK CLC-ODS (5 μm, 6.0 mm I.D.×15 cm), mobile phase; $H_2O:CH_3CN:Et_2NM = 60:40:0.2$, Flow rate; 1.5 ml/min, detector; UV(254 nm)]. The radiochemical yield was approximately 50% based on tritium-labeled 2-piperazinyl-quinoline.

The specific activity of [$^3$H]6-nitroquipazine was determined by high performance liquid chromatograhy and liquid scintillation counter. The specific activity of [$^3$H]6-nitroquipazine was 2.26 TBq/mmol. The radiochemical purity of [$^3$H]6-nitroquipazine was more than 95% from high performance liquid chromatography and thin layer chromatography.

EXAMPLE 2

[$^3$H]6-Nitroquipazine Binding

Method

Rats were killed by decapitation and the brains (minus cerebellum, pons medulla and oblongata) were rapidly removed. The brain tissue was homogenized in 50 volumes of ice-cold buffer (50 mM Tris-HCl, 120 mM NaCl, 5 mM KCl, pH 7.4) with a Kinematica Polytron homogenizer at setting 5 for 30 seconds. The homogenate was centrifuged at 48,000×g for 10 minutes. The resulting pellet was resuspended in 50 volumes of ice-cold buffer and recentrifuged. The final pellet was resuspended in the same 50 volumes of buffer.

Aliquots of membrane suspension were incubated with [$^3$H]6-nitroquipazine (30–1,200 pM) at 22° C. for 2 hours for the equilibrium saturation. After the addition of 4 ml of ice-cold buffer the homogenates were rapidly filtered through Whatman GF/C filters pretreated with 0.05% polyethleneimine. The filters were washed with ice-cold buffer (3×5 ml). The radioactivity trapped by the filters was determined by a liquid scintillation counter. Non-specific binding was estimated in the presence of 1 μM of paroxetine.

Results

Figure 2:
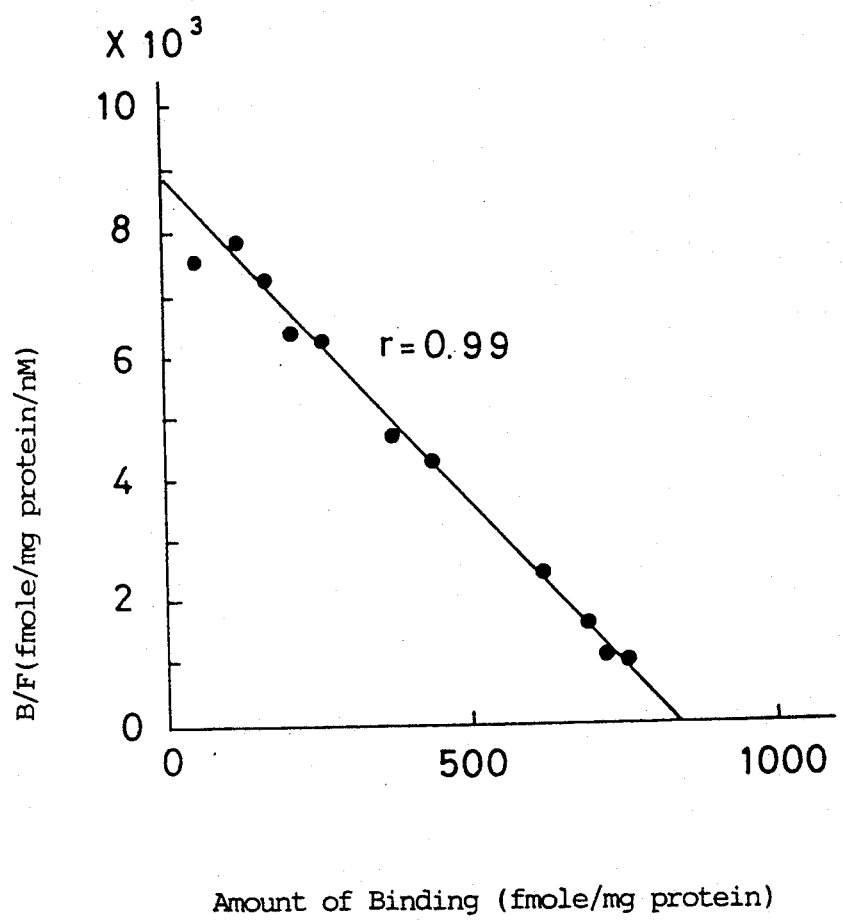
FIG. 2 shows the Scatchard plot analysis of [$^3$H]6-nitroquipazine binding.

[$^3$H]6-Nitroquipazine bound with high affinity to rat brain membranes in a saturable and reversible fashion (FIG. 1). At equilibrium, specific binding of [$^3$H]6-nitroquipazine represented 95% of the total binding at a [$^3$H]6-nitroquipazine concentration of 110 pM, as shown in FIG. 1. Scatchard analysis [Scatchard G.; Ann. NY Acad. Sci., 51, 660–672 (1949)] of equilibrium-saturation binding data indicated a single population of binding sites with an apparent equilibrium dissociation constant ($K_d$) of 93 pM and a maximal number of binding sites ($B_{max}$) of 832 fmol/mg protein (FIG. 2).

EXAMPLE 3

Effect of Several Drugs on [$^3$H]6-Nitroquipazine Binding

Method

The inhibition of [$^3$H]6-nitroquipazine binding by several drugs was studied at 0.12 nM [$^3$H]6-nitroquipazine. Ten different concentrations of the drugs were used for each determination. Aliquots of membrane suspension were incubated with [$^3$H]6-nitroquipazine at 22° C. for 2 hours. The specific binding of [$^3$H]6-nitroquipazine was determined as described in Example 2.

$K_i$ values for each drug were calculated using the formula $K_i = IC_{50}/(1 + C/K_d)$, where $IC_{50}$ is the concentration causing a 50% inhibition of specific binding, C is the concentration of [$^3$H]6-nitroquipazine used and $K_d$ is the equilibrium dissociation constant. Drug $IC_{50}$ values were defined by means of the iterative non-linear least-squares method.

Results

Table 1 shows the $K_i$ values of several drugs on [$^3$H]6-nitroquipazine binding. Low $K_i$ values show the potent inhibitory effect on [$^3$H]6-nitroquipazine binding.

TABLE 1

| Drugs | Ki (nM) |
|---|---|
| 6-Nitroquipazine | 0.128 |
| Paroxetine | 0.171 |
| Indalpine | 1.931 |
| Fluoxetine | 6.610 |
| Z-Norzimelidine | 7.926 |
| Imipramine | 14.40 |
| Amitriptyline | 15.97 |
| Z-zimelidine | 61.99 |
| Nortriptyline | 89.46 |
| E-Norzimelidine | 120.3 |
| Desipramine | 143.2 |
| E-Zimelidine | 624.4 |
| Mianserin | 7418.7 |
| Maprotiline | 10227.9 |
| Serotonin | 426.2 |

As shown in Table 1, the non-tricyclic serotonin uptake inhibitors (6-nitroquipazine, paroxetine, indalpine, fluoxetine and Z-norzimelidine) gave $K_i$ values in the low nanomolar ranges for inhibition of [$^3$H]6-nitroquipazine binding. The tricyclic antidepressants (imipramine, amitriptyline, nortriptyline and desipramine) inhibited potently the [$^3$H]6-nitroquipazine binding. Of the drugs examined, 6-nitroquipazine was the most potent in inhibiting [$^3$H]6-nitroquipazine binding, and was more potent than paroxetine and imipramine. Other drugs (yohimbine, scopolamine, propranolol, haloperidol, diazepam) gave $K_i$ values greater than 1 μM, and no inhibition of [$^3$H]6-nitroquipazine binding could be demonstrated with other neurotransmitters (dopamine, norepinephrine, histamine, GABA).

Figure 3:
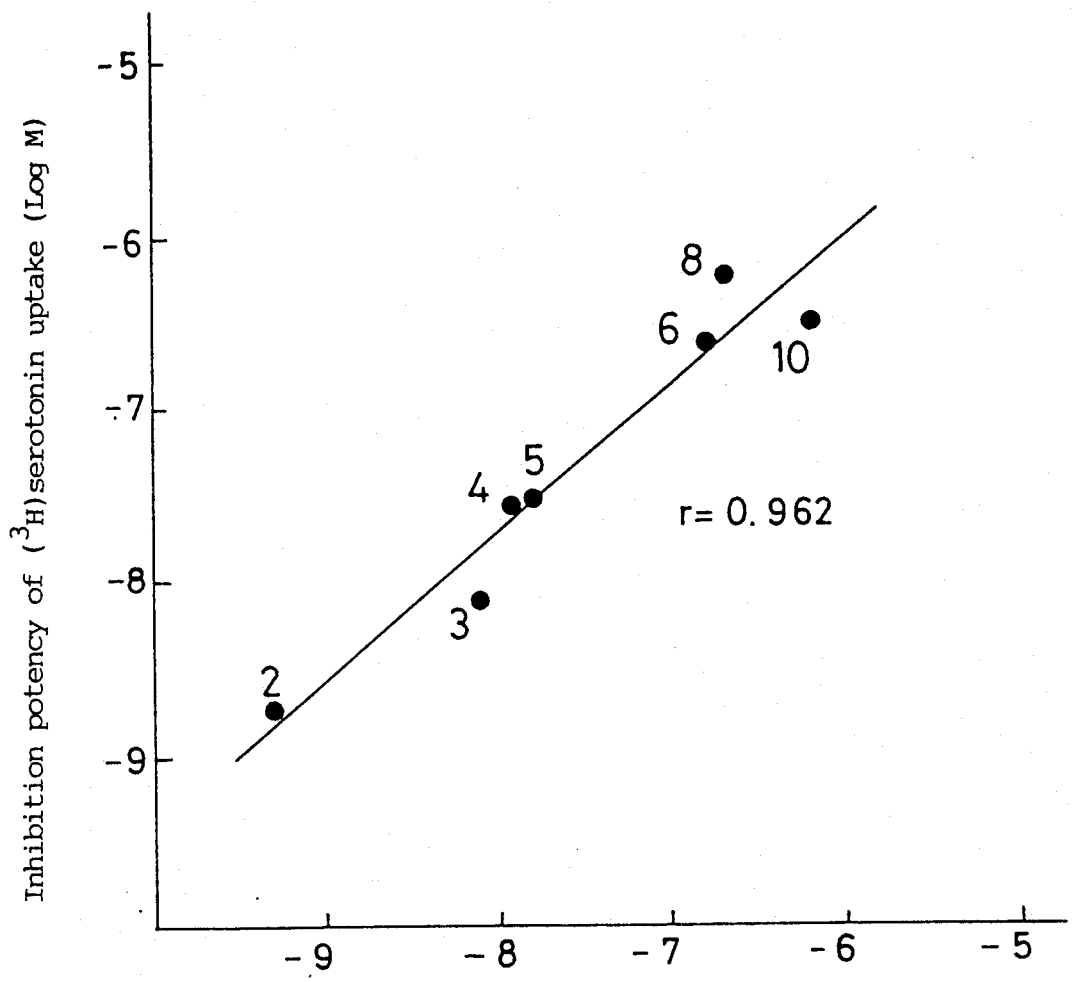
FIG. 3 shows the correlation between the potency of various drugs to inhibit [$^3$H]6-nitroquipazine binding and to inhibit [$^3$H]serotonin uptake.

The potencies of various drugs to inhibit [$^3$H]6-nitroquipazine binding to rat brain membranes correlated with their inhibitory effect on [$^3$H] serotonin uptake into rat brain synaptosomes [Hyttel, J.; Prog. Neuro-Psychopharmacol. Biol. Psychiat., 6, 277-295 (1982)]. As shown in FIG. 3, a correlation coefficient of 0.962 was obtained, which was highly significant ($P<0.001$).

EXAMPLE 4

Effects of Serotonin Neuronal Lesions with P-Chloroamphetamine

Method

Rats were injected i.p. three times (24 hours interval) with p-chloroamphetamine (2.5 mg/kg), and were decapitated 7 days after final injection. The cerebral cortex of rat brain was rapidly dissected, and [$^3$H]6-nitroquipazine binding to cerebral cortical membranes was examined as described previously.

Results

The results are shown in Table 2.

TABLE 2

|  | Bmax (fmole/mg protein) mean ± S.B.M. | kd (nM) mean ± S.E.M. |
|---|---|---|
| Control | 616.0 ± 64.4 | 0.141 + 0.01 |
| Treated with chloroamphetamine | 170.5 ± 44.8*** | 0.108 ± 0.01* |

*$P < 0.01$. ***$P < 0.001$ (based on control)

Table 2 shows the effects of p-chloroamphetamine on [$^3$H]6-nitroquipazine binding to cortical membranes. The [$^3$H]6-nitroquipazine binding to cortical membranes prepared from the lesioned rats decreased 72% compared to controls. However, the $K_d$ values were slightly decreased in lesioned rats. The content of serotonin and 5-hydroxyindoleacetic acid in the cerebral cortex of lesioned rats was 0.129±0.037 ng/mg tissue and 0.0541±0.008 ng/mg tissue, respectively. The content of serotonin and 5-hydroxyindoleacetic acid in the control rats was 0.3362±0.037 ng/mg tissue and 0.2123±0.038 ng/mg tissue, respectively.

EXAMPLE 5

Regional Distribution of [$^3$H]6-Nitroquipazine Binding in Rat Brain

Method

Rats were killed by decapitation and the brains were dissected (cerebral cortex, striatum, hippocampus, hypothalamus, midbrain, cerebellum, pons medulla and oblongata) on ice. [$^3$H]6-Nitroquipazine binding was estimated as described previously.

Results

Results are shown in Table 3.

TABLE 3

| Regions | Bmax (fmole/mg protein |
|---|---|
| Hypothalamus | 1211.8 ± 33.2 |
| Midbrain | 1107.8 ± 30.2 |
| Striatum | 807.4 ± 41.5 |
| Hippocampus | 612.2 ± 35.4 |
| Medulla oblongata | 598.2 ± 25.6 |
| Cortex | 565.6 ± 28.3 |
| Cerebellum | 91.2 ± 4.0 |

As shown in Table 3, specific [$^3$H]6-nitroquipazine binding was highest in the hypothalamus and midbrain. Binding was moderately high in the striatum, hippocampus, medulla oblongata and cerebral cortex, and was lowest in the cerebellum.

The specific binding sites labeled by [$^3$H]6-nitroquipazine used in the present invention are associated with the serotonin uptake sites as follows.

(1) As shown in Example 3, [$^3$H]6-nitroquipazine binding was selectively inhibited by selective serotonin uptake inhibitors. Good correlation between the potency of various drugs to inhibit [$^3$H]6-nitroquipazine binding and to inhibit [$^3$H]serotonin uptake was shown.

(2) As shown in Example 5, the regional distribution of [$^3$H]6-nitroquipazine binding in the rat brain had close correlation with that found previously.

(3) As shown in Example 4, the destruction of serotonin neuron terminals by p-chloroamphetamine resulted in decreases in endogenous serotonin levels and [$^3$H]6-nitroquipazine binding.

The radioligand used in this invention is more potent than [$^3$H]imipramine and [$^3$H]paroxetine which have been used widely. Therefore, [$^3$H]6-nitroquipazine is a suitable radioligand for studying the serotonin uptake sites in brains and platelets from patients with depression or other psychiatric and non-psychiatric illnesses which involve the serotonin system.

What is claimed is:

1. An improved method for measurement of serotonin uptake sites in a sample, in which a radioligand is incubated with a sample and then the radioactivity of the radioligand bound to the sample is determined, wherein the improvement comprises using tritium-labeled 6-nitro-2-N-piperazinylquinoline of the following formula:

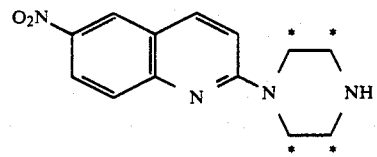

wherein
tritium is substituted at one or more of the asterisks or an acid addition salt thereof as the radioligand.

2. A radioligand for measuring serotonin uptake sites in a sample, which comprises tritium-labeled 6-nitro-2-N-piperazinylquinoline of the following formula:

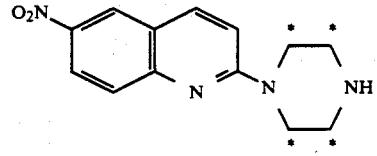

wherein asterisks indicate positions for the tritium; or an acid addition salt thereof.

* * * * *